(12) United States Patent
von Arx et al.

(10) Patent No.: US 11,426,594 B2
(45) Date of Patent: Aug. 30, 2022

(54) INTRACARDIAC PACEMAKER DEVICE, PARTICULARLY FOR VDD OR VDDR PACING

(71) Applicant: BIOTRONIK SE & Co. KG, Berlin (DE)

(72) Inventors: Jeffrey A. von Arx, Lake Oswego, OR (US); Wantjinarjo Suwito, West Linn, OR (US); Brian M. Taff, Portland, OR (US); Eric Austin, Portland, OR (US); Hannes Kraetschmer, West Linn, OR (US); Min Qu, Wilsonville, OR (US); Isaac Kreft, Hillsboro, OR (US); Dirk Muessig, West Linn, OR (US); Larry Stotts, Tigard, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 197 days.

(21) Appl. No.: 16/251,265

(22) Filed: Jan. 18, 2019

(65) Prior Publication Data
US 2019/0240496 A1 Aug. 8, 2019

Related U.S. Application Data

(60) Provisional application No. 62/626,699, filed on Feb. 6, 2018.

(51) Int. Cl.
*A61N 1/375* (2006.01)
*A61N 1/365* (2006.01)
(Continued)

(52) U.S. Cl.
CPC ......... *A61N 1/37512* (2017.08); *A61N 1/057* (2013.01); *A61N 1/3622* (2013.01);
(Continued)

(58) Field of Classification Search
CPC .. A61N 1/37512; A61N 1/057; A61N 1/3622; A61N 1/3684; A61N 1/3756; A61N 1/378
See application file for complete search history.

(56) References Cited

U.S. PATENT DOCUMENTS

2011/0190842 A1\* 8/2011 Johnson ................. A61N 1/375
607/37
2013/0123875 A1\* 5/2013 Varady ................. A61N 1/3968
607/36

(Continued)

OTHER PUBLICATIONS

European Office Action dated Jul. 30, 2020, of the corresponding European Patent App. No. EP 18 171 578.0 (5 pages).

*Primary Examiner* — Unsu Jung
*Assistant Examiner* — Adreanne A. Arnold
(74) *Attorney, Agent, or Firm* — Buchanan Ingersoll & Rooney PC

(57) ABSTRACT

An intracardiac pacemaker device, comprising a housing that is configured to be implanted entirely within a ventricle (V) of a heart (H), an electronic module for generating pacing pulses, a battery for supplying energy to the electronic module, an elongated lead extension protruding from the housing, at least a first electrode arranged on the elongated lead extension, and a pacing electrode and a return electrode for applying the pacing pulses to cardiac tissue, wherein the pacing electrode is arranged on the housing. The electronic module is electrically coupled to the pacing electrode via the housing, and wherein the electronic module is configured to carry out measurements of electrical activity via the at least one first electrode of the elongated lead extension.

15 Claims, 15 Drawing Sheets

(51) Int. Cl.
   *A61N 1/368*   (2006.01)
   *A61N 1/362*   (2006.01)
   *A61N 1/05*    (2006.01)
   *A61N 1/37*        (2006.01)
   *A61N 1/378*       (2006.01)

(52) U.S. Cl.
   CPC ....... *A61N 1/3684* (2013.01); *A61N 1/36521* (2013.01); *A61N 1/3754* (2013.01); *A61N 1/3756* (2013.01); *A61N 1/3627* (2013.01); *A61N 1/3688* (2013.01); *A61N 1/36585* (2013.01); *A61N 1/3702* (2013.01); *A61N 1/3787* (2013.01)

(56) References Cited

U.S. PATENT DOCUMENTS

| | | | | |
|---|---|---|---|---|
| 2016/0129239 | A1* | 5/2016 | Anderson | A61M 25/09 606/129 |
| 2016/0310723 | A1* | 10/2016 | Eggen | A61N 1/3756 |
| 2016/0310726 | A1* | 10/2016 | Demmer | A61N 1/057 |
| 2016/0315302 | A1* | 10/2016 | Aamodt | A61N 1/3752 |
| 2018/0028814 | A1 | 2/2018 | Ghosh | |
| 2019/0054304 | A1* | 2/2019 | Maile | A61N 1/3756 |

* cited by examiner

INTRACARDIAC PACEMAKER DEVICE, PARTICULARLY FOR VDD OR VDDR PACING

CROSS-REFERENCE TO RELATED APPLICATIONS

This patent application claims the benefit of and priority to U.S. Provisional Patent Application No. 62/626,699, filed on Feb. 6, 2018, which is hereby incorporated by reference in its entirety.

TECHNICAL FIELD

The disclosure relates to an intracardiac pacemaker device, particularly for VDD or VDDR pacing.

BACKGROUND

Currently all intracardiac pacing systems (e.g., leadless pacemakers) on the market support only VVI-R therapy, i.e., detection and stimulation in the ventricle in inhibited mode.

However, VDD (stimulation in the ventricle and dual detection, i.e., in the atrium and ventricle in dual mode, i.e., inhibited and triggered), particularly VDDR (i.e., with additional rate modulation) is seen as superior to VVI-R because it gives the patient the hemodynamic benefits of AV synchrony.

The present invention is directed at overcoming one or more of the above-mentioned problems.

SUMMARY

It is an objective to provide an architecture for an intracardiac pacemaker device that allows stimulation of cardiac tissue using VDD and VDDR.

Therefore, according to claim 1, an intracardiac pacemaker device is disclosed, comprising:
  an (e.g., hermetic) housing that is configured to be implanted entirely within a ventricle of a heart,
  an electronic module for generating pacing pulses,
  a battery for supplying energy to the electronic module,
  an elongated lead extension protruding from the housing (e.g., along an axial direction of the housing),
  at least a first electrode arranged on the elongated lead extension, and
  a pacing electrode and a return electrode for applying said pacing pulses to cardiac tissue, wherein the pacing electrode is arranged on the housing,
  wherein the housing forms a conductor via which the electronic module is electrically coupled to the pacing electrode, and wherein the electronic module is configured to carry out measurements of electrical activity (e.g., in an atrium of the heart associated to said ventricle) via the at least one first electrode of the elongated lead extension.

Thus, a practical intracardiac pacing system is proposed with a lead for sensing in the atrium. Due to the fact that the housing acts as a conductor to connect the electronic module (pulse generation) to the pacing electrode, particularly only one feedthrough array is required in an embodiment at the proximal end of the hermetic housing. No tunneling through the battery or wires outside the hermetic housing by-passing the battery are required.

Particular embodiments are stated in the dependent claims and are described below.

Particularly, the first electrode can be arranged at an end of the elongated lead extension for sensing in the atrium. Thus, the lead extension may be configured to extend from the right ventricle via the tricuspid valve into the right atrium such that the at least one electrode is located in the right atrium when the housing is implanted into the right ventricle.

Particularly, the elongate lead extension is flexible so that it can be easily passed through the valve into the atrium.

Furthermore, according to an embodiment of the intracardiac pacemaker device, the housing is partly coated with an electrically insulating material, wherein particularly the material is one of: a bio-compatible material, parylene, or a silicone.

According to a further embodiment of the intracardiac pacemaker device, the hermetic housing comprises a proximal end and a distal end, wherein particularly the pacing electrode is arranged on the distal end of the housing, and/or wherein the elongated lead extension protrudes from the proximal end of the housing. Here, the notions proximal and distal relate to the spatial position of the housing of the pacemaker device with respect to the physician upon implantation of the intracardiac pacemaker device. Particularly, when the housing is implanted into the (e.g., right) ventricle of the heart, the proximal end is located closer to the (tricuspid) valve than the distal end.

Furthermore, according to an embodiment, the battery is arranged in the housing at the distal end of the housing. Furthermore, according to another embodiment, the electronic module is arranged in the housing at the proximal end of the housing.

Furthermore, according to an embodiment, the housing of the pacemaker device is formed by a separate electronics housing that may be hermetically sealed and encloses the electronic module and a separate battery housing of the battery that can be hermetically sealed, too, wherein the electronics housing is connected to the battery housing (e.g., by means of a welding seam or another suitable connection), and wherein the electronics housing forms a proximal portion of the housing of the pacemaker device comprising said proximal end of the housing of the pacemaker device, and wherein the battery housing forms a distal portion of the housing of the pacemaker device comprising said distal end of the housing.

Particularly, the electronics housing and/or the battery housing comprises or is made of titanium. In one embodiment, the housing of the intracardiac pacemaker device comprises or is made of titanium.

Further, in an embodiment, the battery comprises a first and a second terminal connected to the electronic module, respectively, wherein the first terminal is formed by the battery housing itself and the second terminal is formed by a feedthrough pin, which feedthrough pin is electrically isolated from the battery housing by a feedthrough insulation.

Particularly, according to an embodiment, the first terminal is a negative terminal of the battery and the second terminal is a positive terminal of the battery.

Further, particularly, according to an embodiment, said feedthrough pin (second terminal) is located at a proximal end of the battery housing opposite the distal end of the battery housing where the pacing electrode is located. This allows the second terminal to make a connection to the electronic module inside the hermetic housing of the pacemaker device (e.g., near the welding seam) where the battery is closest to the electronic module.

Furthermore, in an embodiment, a connection between the first terminal (e.g., negative battery connection) and the electronic module is also arranged at the proximal end of the battery housing near said feedthrough pin (second terminal).

Thus, the pacemaker device according to the above-stated embodiments is therefore different from the usual intracardiac pacemaker device according to the state of the art, where the battery is arranged at the proximal end of the hermetic housing, the electronic module is located at the distal end of the hermetic housing, the pacing electrode is electrically isolated from the hermetic housing (and located at distal end of housing), and where a single feedthrough design is usually employed with the feedthrough located at the distal end of the housing to connect the pacing electrode to the electronic module.

However, with this standard construction, an intracardiac pacemaker with a lead extension for sensing in the atrium is difficult to construct. The difficulty lies in the fact that the feedthrough to the pacing electrode is at the distal end of the housing, but the lead extension for sensing in the atrium naturally should connect to the proximal end of the housing. Using the known mechanical characteristics for intracardiac pacing systems, there are two ways to electrically connect the sense electrodes in the atrial lead extension to the electronic module. First, feedthroughs can be incorporated at both ends of the housing (distal end for the pacing electrode and proximal end for the atrial sense electrodes), but the proximal end of the housing in known solutions contains the battery. Thus, some sort of tunnel through the battery or along the side of the battery is required to connect the feedthroughs of the atrial sense electrode(s) to the electronic module. This would be expensive to implement, and would reduce battery capacity (as the tunnel would reduce active battery volume). A second mechanical construction would incorporate all feedthroughs distal to the battery, and use a wire outside of the hermetic enclosure to interconnect the proximal atrial sensing lead to the electronics module. This would increase the size of the implantation catheter (as it would now need to accommodate the intracardiac pacing system and the interconnect wires), and might lead to reliability concerns.

The solution according to the present invention avoids these technically involved designs by using the housing as a conductor to connect the pacing electrode to the electronic module. Feedthroughs for the return electrode and the at least one electrode of the elongate lead extension can then be located at the proximal end of the housing without requiring installation volume along the battery or external wiring.

Furthermore, according to an embodiment, the intracardiac pacemaker device comprises a second electrode arranged on the elongated lead extension, wherein particularly the electronic module is configured to carry out measurements of electrical activity via the at least one first electrode and said second electrode of the elongated lead extension.

Further, according to an embodiment, the intracardiac pacemaker device comprises a plurality of electrodes arranged on the elongated lead extension for atrial sensing, wherein the electronic module is configured to carry out measurements of electrical activity using said plurality of electrodes or a selection thereof.

Furthermore, according to an embodiment of the intracardiac pacemaker device, the return electrode is arranged on the proximal end of the housing, wherein, in an embodiment, the return electrode is electrically isolated from the housing. According to an alternative embodiment, the return electrode is an annular electrode arranged on the elongate lead extension, particularly closer to the proximal end of the housing than the at least one electrode or than the first and a second electrode or than a plurality of electrodes that is/are arranged on the elongated lead extension for atrial sensing.

Furthermore, according to an embodiment, the intracardiac pacemaker device comprises at least two feedthroughs at the proximal end of the housing for electrically connecting the return electrode and the at least one first electrode to the electronic module.

According to a further embodiment, the intracardiac pacemaker device comprises at least three, particularly exactly three, feedthroughs at the proximal end of the housing for electrically connecting the return electrode and the at least one first electrode and the second electrode to the electronic module.

Furthermore, according to yet another embodiment, the intracardiac pacemaker device comprises a plurality of feedthroughs at the proximal end of the housing for electrically connecting the return electrode and said plurality of electrodes of the elongated lead extension to the electronic module.

Furthermore, according to an embodiment, the at least one first electrode, that is e.g., arranged at the end of the elongated lead extension, is configured to apply pacing pulses to cardiac tissue generated by the electronic module.

According to a further embodiment of the intracardiac pacemaker device, the pacing electrode is electrically connected via a pin to the distal end of the housing (e.g., to the battery housing), wherein in an embodiment the pin is a separate pin with respect to the housing that connects to the distal end of the housing (e.g., to the battery housing). According to an alternative embodiment, the pin is integrally formed with the distal end of the housing (e.g., integrally with the distal end of the battery housing).

According to a further alternative embodiment, the pacing electrode is integrally formed with the distal end of the housing (particularly with the distal end of the battery housing), e.g., forms a distal end of the housing, particularly of the battery housing.

Furthermore, according to an embodiment, the intracardiac pacemaker device comprises a tine array for anchoring the housing of the intracardiac pacemaker device to cardiac tissue (e.g., of the right ventricle). Particularly, according to an embodiment, the tine array is arranged on the distal end of the housing. Further, according to an embodiment, the tine array comprises tines protruding from an annular member of the tine array.

Furthermore, the tines can be configured to move under the action of a restoring force from a first configuration in which the tines extend along an axial direction of the housing or annular member to a second configuration in which each tine comprises a hook shape for engaging cardiac tissue. Particularly, the annular member and/or said tines can be formed out of a metal, particularly a super-elastic metal, particularly a super-elastic Nickel-Titanium-Alloy, particularly Nitinol.

Furthermore, according to an embodiment of the intracardiac pacemaker device, the intracardiac pacemaker device comprises an electrically isolating ring element for connecting the tine array to the housing (particularly to the battery housing), which ring element surrounds the pacing electrode, which pacing electrode is arranged in a central opening of the ring element.

Furthermore, according to an embodiment, said the annular member is arranged in the central opening of the ring element. Furthermore, in an embodiment, the annular member is fastened to the electrically isolating ring element by means of an annular locking element that is arranged in the central opening of the ring element and engages with the pacing electrode. Furthermore, in an embodiment, the locking element surrounds the pacing electrode. Further, according to an embodiment, the intracardiac pacemaker device comprises a collar, particularly a collar comprising a steroid, that surrounds an end section of the pacing electrode, which end section protrudes out of the locking element and serves for making contact to cardiac tissue for applying pacing pulses to the ventricle. In one embodiment, the steroid is dexamethasone acetate which is well known to improve both the acute and chronic pacing thresholds of traditional pacing systems with leads.

According to yet another embodiment, an end section of the elongated lead extension comprising the at least one first electrode is configured to be arranged in an atrium of the heart, when the housing is implanted into the associated ventricle of the heart.

Particularly, in an embodiment, the elongated lead extension comprises at least a first wire for electrically connecting the at least one first electrode to the associated feedthrough, and particularly also a second wire for electrically connecting the second electrode to the associated feedthrough, so that the electronic module can conduct atrial sensing via the at least one first and particularly second electrode.

Furthermore, in an embodiment, the elongated lead extension is connected by a locking cap to the proximal end of the housing, wherein particularly the return electrode is an annular electrode that is arranged between the locking cap and an annular electrically isolating washer.

According to a further embodiment of the intracardiac pacemaker device, the elongated lead extension is connected via a tether to an anchor, particularly a deployable and/or self-expandable anchor (e.g., for anchoring in the inferior vena cava or in the superior vena cava or within the atrium), wherein, when the anchor is anchored in the inferior or superior vena cava, the at least one electrode or said two electrodes or said plurality of electrodes of the elongate lead extension are positioned in the atrium when the housing is implanted in the corresponding ventricle, or wherein the elongate lead extension comprises a shape memory alloy wire (e.g., a Nitinol wire) extending at least in a section of the elongate lead extension.

Particularly, according to an embodiment, said section is a proximal section (i.e., a distal section with respect to the housing) of the elongate lead extension, and wherein particularly the shape memory alloy wire is shape set to a curved (particularly partly circular) configuration so that the proximal section of the elongated lead extension particularly partially circumnavigates the atrium when the housing of the intracardiac pacemaker device is implanted into the corresponding ventricle of the heart.

According to an alternative embodiment, the shape memory alloy wire extends throughout an entire length of the elongate lead extension (i.e., at least throughout 90% of said length), wherein the shape memory alloy wire is shape set to be straight or (e.g., slightly) curved so that the elongate lead extension can be extended through an (e.g., tricuspid) valve of the heart into the (e.g., right) atrium when the housing is implanted into the corresponding (e.g., right) ventricle.

Further features, aspects, objects, advantages, and possible applications of the present invention will become apparent from a study of the exemplary embodiments and examples described below, in combination with the Figures, and the appended claims.

DESCRIPTION OF THE DRAWINGS

Further features and embodiments of the present invention shall be described below with reference to the Figures, wherein.

DETAILED DESCRIPTION

Figure 1:
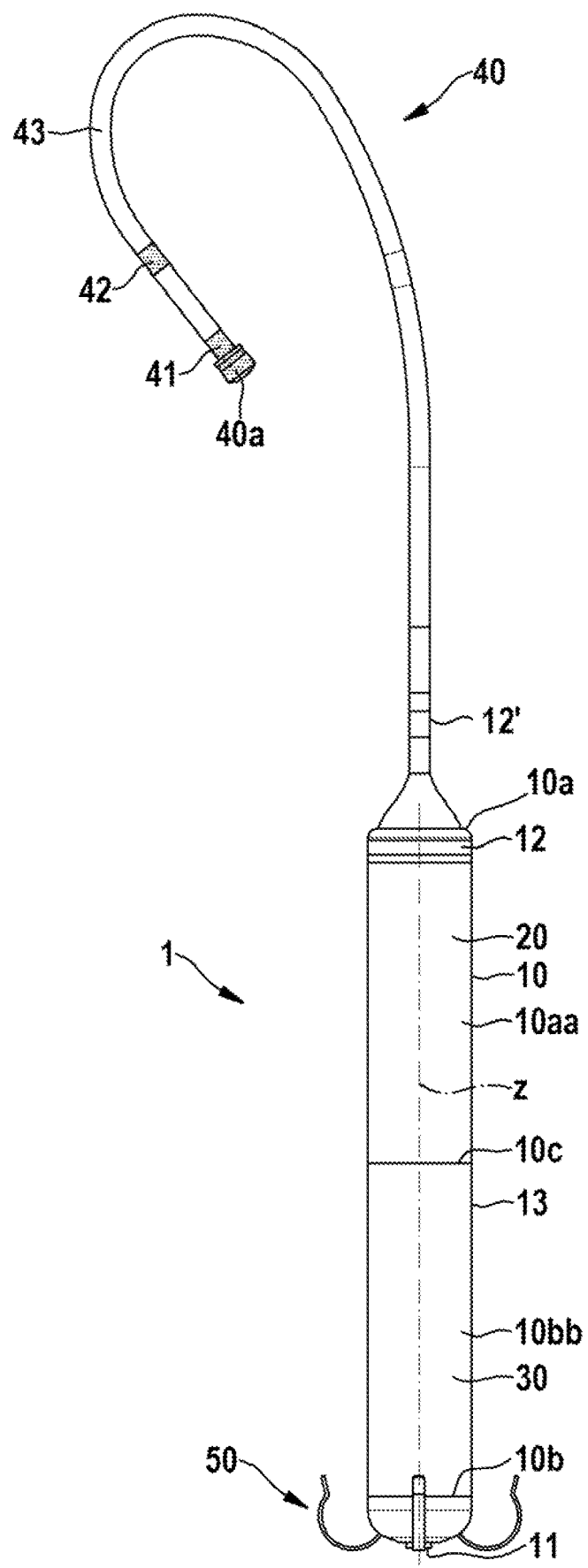
FIG. 1 shows an embodiment of an intracardiac pacemaker device.

The present disclosure relates to an intracardiac pacemaker device that is particularly configured to perform therapy in VDD or VDDR mode. According to FIG. 1, the intracardiac pacemaker device 1 comprises a metallic housing 10 for hermetically encapsulating a battery 30 and an electronic module 20 for generating pacing pulses and for measuring electrical activity in the atrium A of a heart H, wherein the housing 10 is configured for implantation into the corresponding ventricle V of the heart H (here right atrium A and right ventricle V). The housing 10 extends along a longitudinal axis z and comprises a proximal end 10a and an opposing distal end 10b.

Particularly, the battery 30 is arranged in the housing 10, i.e., is arranged in an internal space surrounded and hermetically sealed by the housing 10, wherein the battery 30 is located at the distal end 10b of the housing 10, while the active electronics, i.e., the electronic module 20, is located at the proximal end 10a of the housing 10. In an embodiment, a cylindrical wall of the battery 30 (which may be formed out of titanium) forms a distal portion of the cylindrical wall of the housing 10 of the pacemaker device. In other words, in this embodiment, the housing 10 comprises two separate housings 10aa, 10bb, namely an electronics housing 10*aa* enclosing the electronic module 20 and forming the proximal end 10*a* of the combined housing 10 and a battery housing 10*bb* for hermetically sealing the battery 30, which battery housing 10*bb* forms the distal end 10*b* of the combined housing 10. Thus, the hermetically sealed battery 30 is not put in a second hermetically sealed housing 10, but rather the hermetically sealed battery 30 is part (i.e., a distal portion) of the hermetically sealed housing 10. This maximizes the active battery volume by eliminating a double wall around the battery.

Furthermore, the intracardiac pacemaker device 1 comprises a pacing electrode 11 for delivering pacing pulses to the ventricle V, wherein the pacing electrode 11 is arranged at the distal end 10*b* of the housing 10 (e.g., adjacent to the battery 30), wherein the pacing electrode 11 is electrically connected to the metallic (e.g., titanium) housing 10, and the housing 10 acts as the electrical connection to the electronic module 20.

Figure 2:
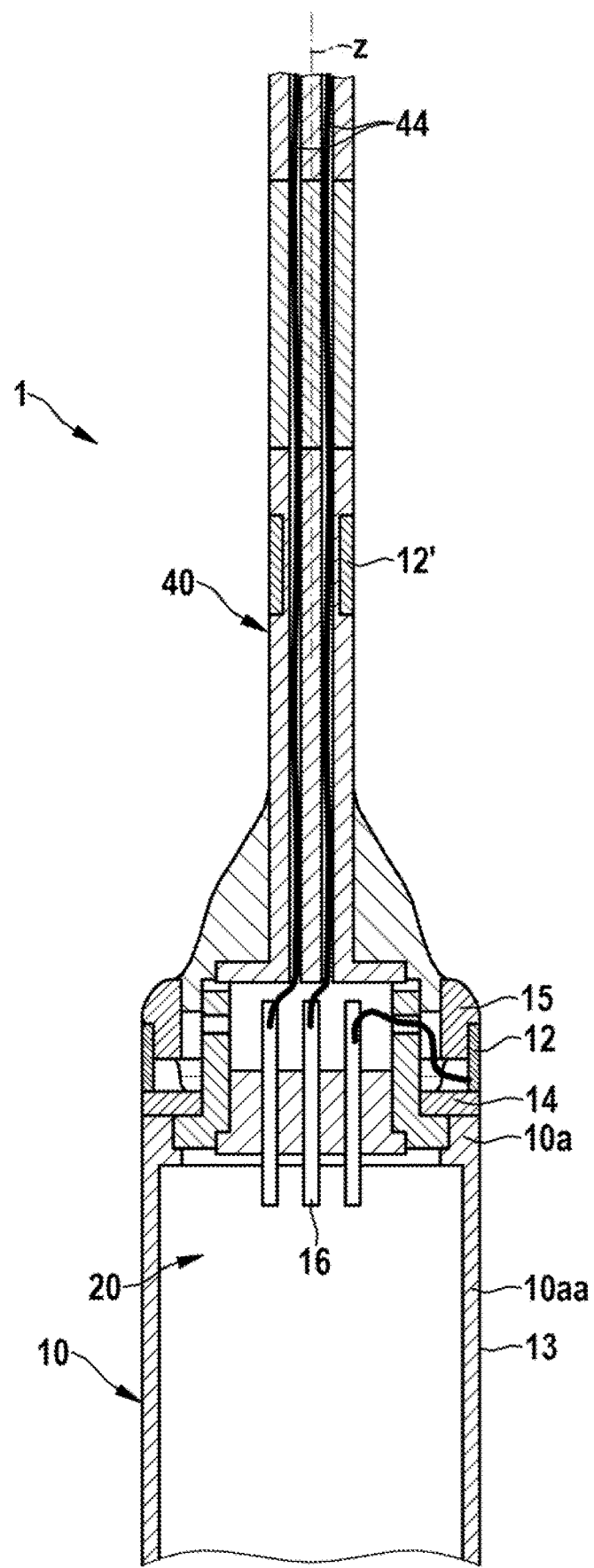
FIG. 2 shows a detail of the elongated lead extension of the intracardiac pacemaker device shown in FIG. 1.

Furthermore, the pacemaker 1 comprises a return electrode (e.g., in form of a ring electrode) 12 that is located on the proximal end 10*a* of the housing 10, and is electrically isolated from the metallic housing 10 of the intracardiac pacemaker device 1, particularly by an electrically isolating washer 14 as shown in FIG. 2. Furthermore, the return electrode 12 can be fixed to the proximal end 10*a* of the housing 10 by means of a locking cap 15 that can also be used to fix an elongated lead extension 40 to the proximal end 10*a* of the housing 10. The lead extension 40 protrudes from said proximal end 10*a* in the axial direction z of the housing 10 and comprises a first electrode 41 and particularly a second electrode 42 in a proximal section 43 of the lead extension 40, which electrodes 41, 42 are connected to the electronic module 20 via wires 44 extending in the lead extension 40. The electronic module 20 is configured to sense electrical activity in the atrium A by means of these electrodes 41, 42. Particularly, the at least one first electrode 41 can be arranged at the end of the lead extension 40. The lead extension 40 is configured to be arranged at least in section (i.e., with the proximal section 43) in the atrium A, when the housing 10 is implanted into the ventricle V, wherein the lead extension 40 extends from the ventricle V through the (tricuspid) valve T to the atrium A.

Figure 4A:
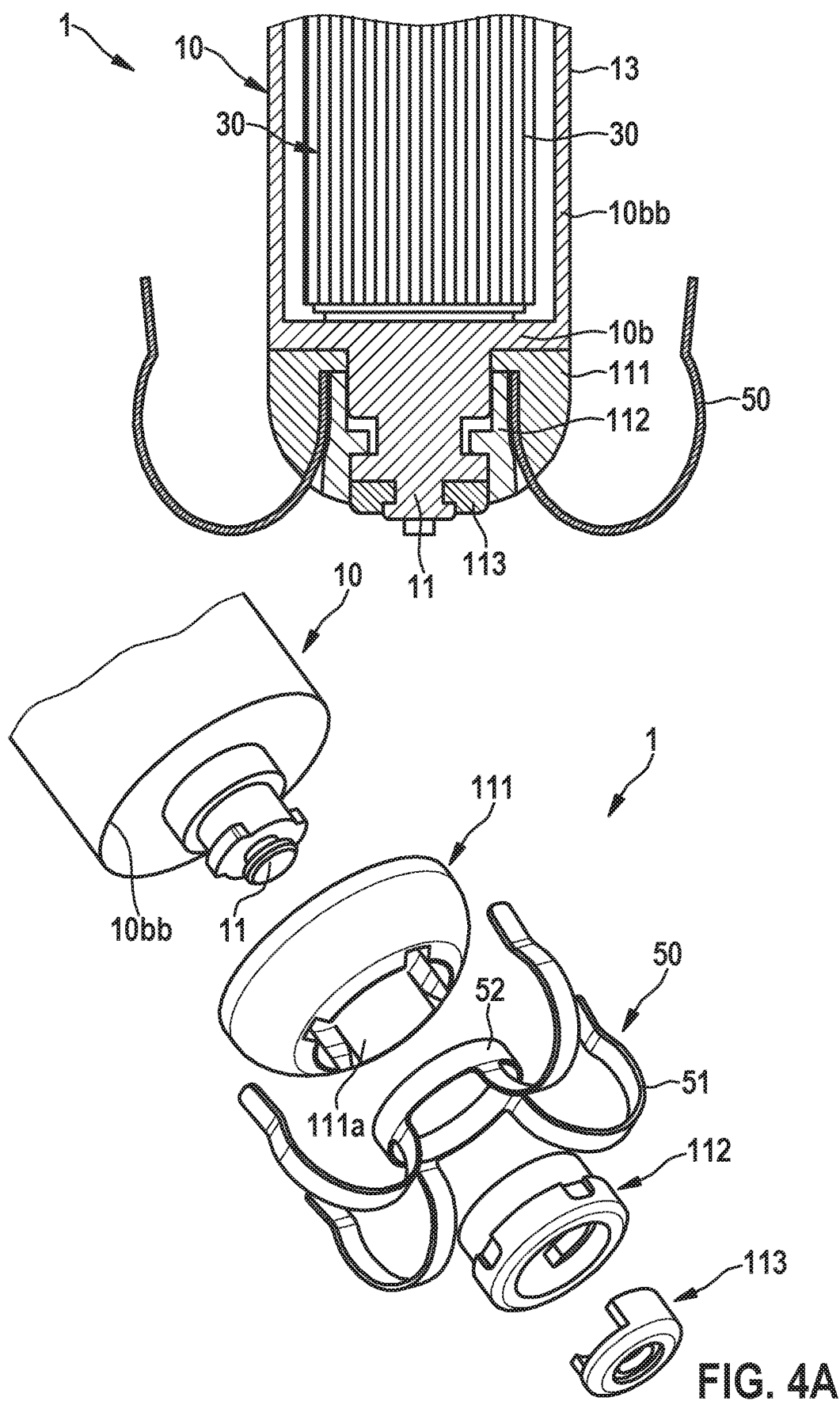
FIG. 4A shows a cross-sectional view as well as an exploded view of an alternative embodiment of the pacing electrode.
Figure 4B:
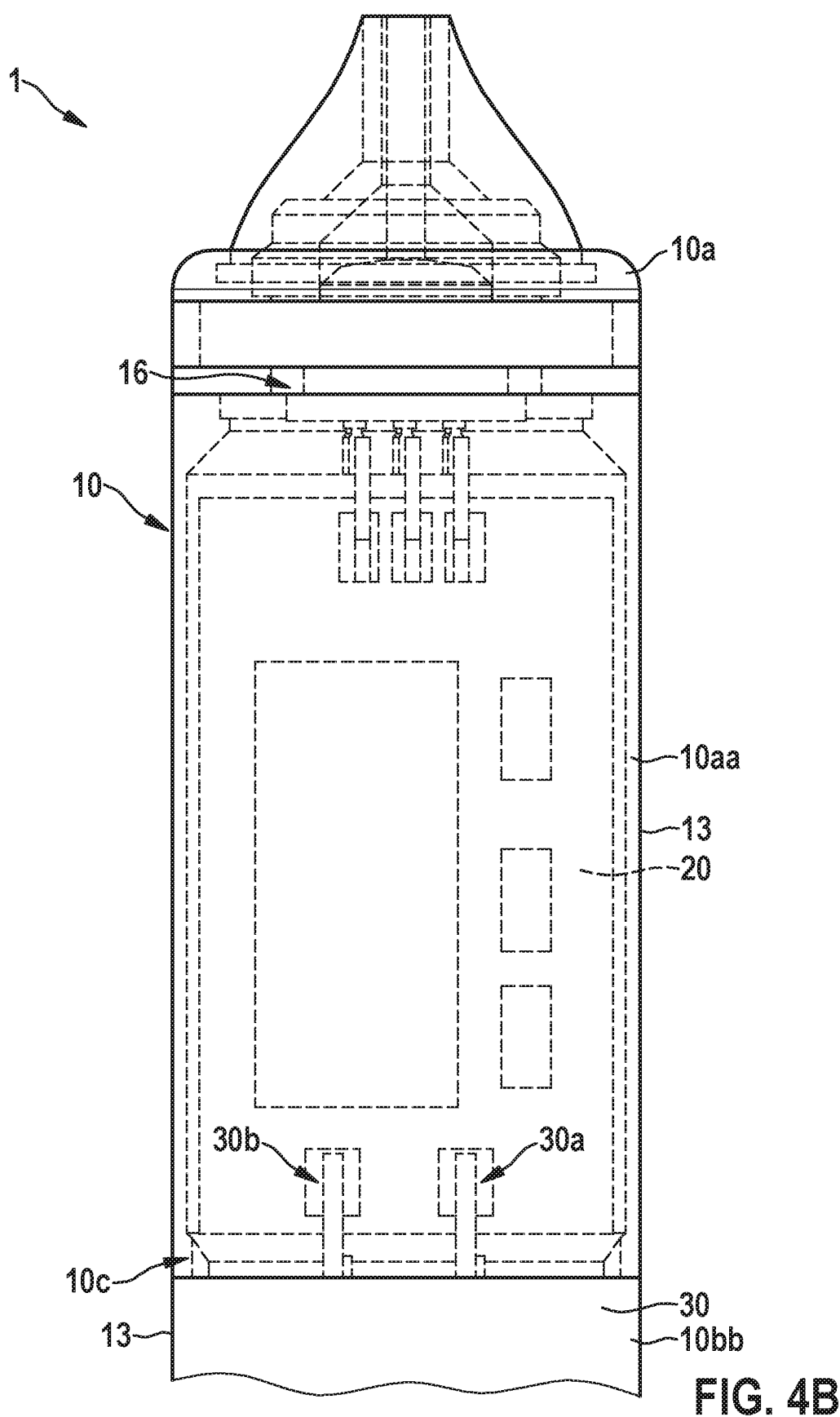
FIG. 4B shows a cross-sectional view of the housing of the pacemaker device which is comprised of a separate electronics housing and a separate battery housing.

Furthermore, according to an embodiment, all electrical feedthroughs 16 of the metallic housing 10 are located on the proximal end 10*a* of the intracardiac pacemaker device 1 (cf. FIGS. 2 and 4B).

Furthermore, the (e.g., titanium) housing 10 is particularly insulated from the tissue of the ventricle V it is implanted in by a thin bio-compatible electrically insulating layer 13 (e.g., parylene in an embodiment, but it can also be silicone, or any other biocompatible insulating material).

Moving the battery 30 to the distal end 10*b* of the hermetic housing 10 in combination with using the hermetic housing 10 to electrically connect the pacing electrode 11 to the electronic module 20 avoids the challenge of having to run separate electrical connections past the battery as would be needed with conventional intracardiac pacemaker architectures. Only one electrical connection needs to be made at the distal end of the battery 30, and that is a connection to the pacing electrode 11. In the architecture disclosed here the single connection bypassing the battery 30 is made by the titanium housing 10 (particularly by the battery housing 10*bb*) of the hermetic enclosure that is electrically connected to the pacing electrode.

Particularly, according to FIGS. 4A and 4B, the battery 30 is hermetically sealed, and has two terminals 30*a*, 30*b*, one is the (e.g., titanium) battery housing 10*bb* itself (which is the negative terminal in one embodiment) and the other is a feedthrough pin 30*b*, electrically isolated from the battery housing 10*bb* by a feedthrough insulation. The feedthrough pin 30*b* is located at the proximal end of the battery 30, (the opposite end of the battery as the pacing electrode 11). This allows the battery positive terminal 30*b* to make a connection to the module 20 inside hermetic housing 10 near the seam 10*c* where the battery 30 is closest to the module 20. The negative battery connection is simply an internal connection from the electronic module to the battery housing 10*bb* inside of the hermetic housing 10.

Figure 3:
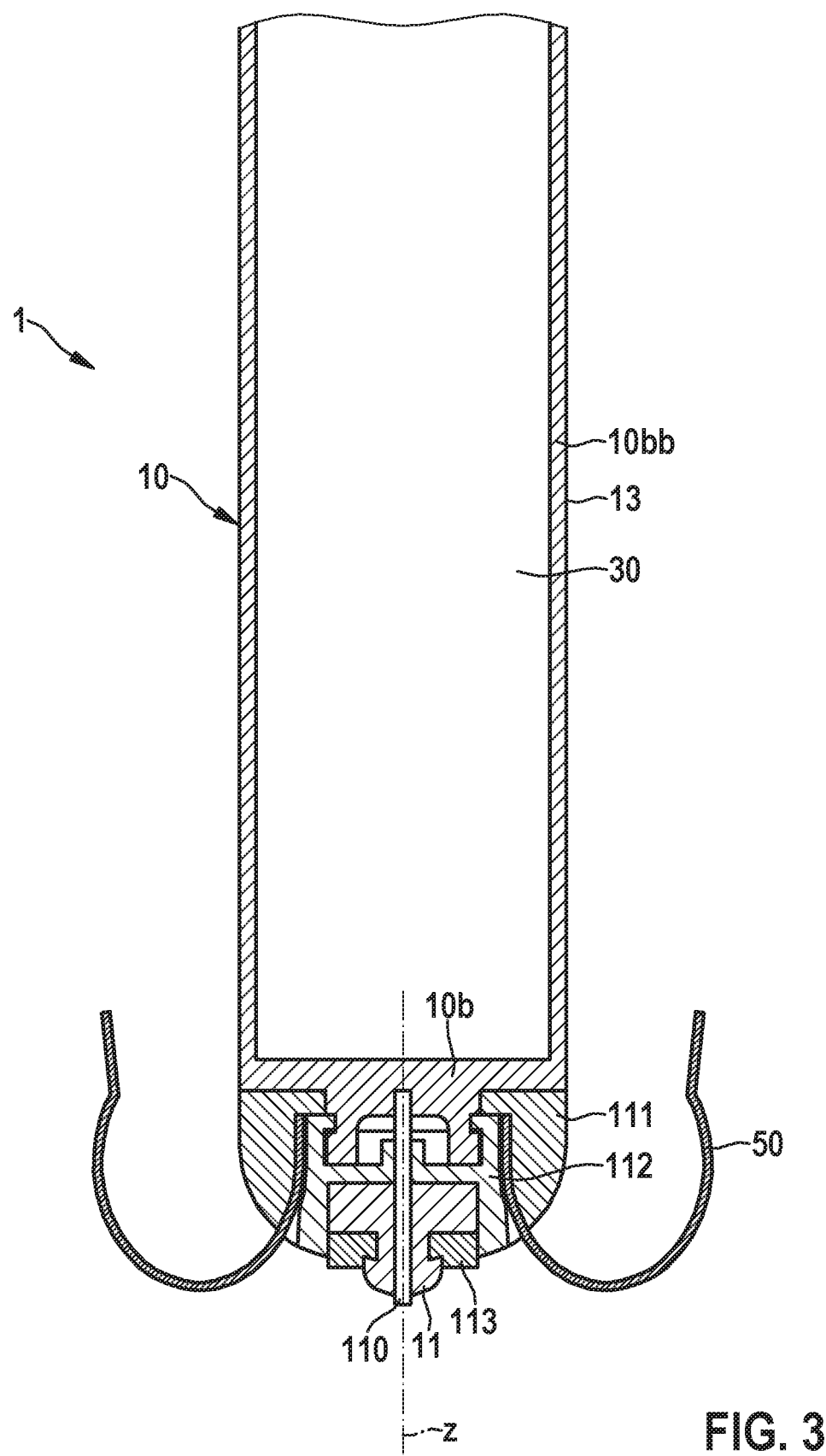
FIG. 3 shows a detail of an embodiment of the pacing electrode at the distal end of a housing of the intracardiac pacemaker device.

According to FIG. 3, the pacing electrode 11 can be electrically connected to the housing 10 by means of a pin 110 that extends in the axial direction z. Further, the pacemaker 1 can comprise a tine array 50 comprising multiple tines 51 connected to an annular member 52 (cf. FIGS. 4A and 4B) which is connected via an electrically isolating ring element 111 to the distal end 10*b* of the housing. Particularly, the annular member 52 is fastened to the electrically isolating ring element 111 by means of an annular locking element 112 that is arranged in the central opening 111*a* of the ring element 111 and engages with the pacing electrode 11. Furthermore, in an embodiment, the locking element 111 surrounds the pacing electrode 11. Further, according to an embodiment, the intracardiac pacemaker device 1 comprises a collar 113, particularly a collar comprising a steroid, that surrounds an end section of the pacing electrode 11, which end section protrudes out of the locking element 112 and serves for making contact to cardiac tissue for applying pacing pulses to the ventricle V. In one embodiment the steroid is dexamethasone acetate which is well known to improve both the acute and chronic pacing thresholds of traditional pacing systems with leads.

Further, in a further embodiment, the pin 110 shown in FIG. 3 is eliminated by including the pin 110 as an integral part of the housing 10. This simplifies the assembly of the device 1 and reduces cost. In another embodiment the entire pacing electrode 11 is an integral part of the housing 10 as shown in FIG. 4A. In this embodiment the pacing electrode 11 can be a surface restructured Ti (this is done to optimize the charge injection capacity of the electrode) or the pacing electrode 11 can be coated with a separate material that has a high charge injection capacity such as IrOx (Iridum Oxide) or TiN (Titanium Nitride). In FIG. 4A the tine array 50 can be connected to the proximal end 10*b* as described above in conjunction with FIG. 3.

Locating the battery 30 at the distal end 10*b* of the hermetic housing 10 also improves the mechanical stability of the implant 1. This is because the battery 30 has the highest mass density of the entire intracardiac pacing system 1. Locating the highest mass density component right by the tine array 50 helps to minimize the rocking movement of the implant 1 during the cardiac cycle (due to the implants center of mass being closer to the anchor point). It also helps to minimize the momentum that the implant 1 has should the proximal end collide with cardiac tissue during the cardiac cycle (this helps to minimize bruising potential).

The battery 30 can either be case negative, case positive, or case neutral. In the preferred embodiment it is case negative. Since the battery housing 10*bb*/housing 10 is electrically shorted to the pacing electrode 11, pacing in a battery case negative design is achieved by the electronic module 20 putting a positive potential on the return electrode 12, rather than the more conventional pacing architecture where the electronics puts a negative potential on the pacing electrode. To cardiac tissue this changes nothing since the tissue only responds to a potential difference between the pacing electrode 11 and the return ring 12. In a case positive battery design, pacing is achieved by the circuitry 20 putting an even higher potential on the return electrode/ring 12 such that the difference in potential between the pacing electrode 11 and the return ring 12 is the desired pacing amplitude. In a case neutral design, a more conventional pacing circuit can be used, but a case neutral battery has a slightly lower energy density since the case insulation reduces available capacity in the battery 30. The reduction in capacity of a case neutral battery is negligible for a conventional sized pacemaker battery, but for a minimal sized battery in an intracardiac pacing system it can be significant.

As shown in FIGS. 1-2, the return (e.g., ring) electrode 12, 12' can be either located in an electrically isolated section at the proximal end 10a of the hermetic housing 10 (ref. 12), or it can be located as a ring on the lead extension 40 close to the hermetic housing 10 (ref. 12'). Both options are illustrated in FIGS. 1-2. In general the closer the return ring 12, 12' is to the pacing electrode 11, the less sensing will be unwanted noise, so locating the ring/return electrode 12 at the proximal end of the hermetic housing 10 is preferred from a signal processing perspective.

In another embodiment, there are three feedthroughs 16 as shown in FIGS. 2 and 4B, all located at the proximal end 10a of the hermetic housing 10. Two of these three feedthroughs 16 electrically connected to the sensing rings 41, 42 in the atrium A, and one connects to the return electrode 12. As already mentioned, the connection to the pacing electrode 11 does not require a feedthrough, and rather is made via the titanium of the hermetic housing 10 itself.

In an alternative embodiment, sensing in the atrium A is done with just one electrode 41 in the atrium A sensing with respect to the return ring 12. This system would have two (rather than three) feedthroughs 16, but this embodiment would likely pick up more electrical noise due to the longer sensing vector length. In a third embodiment there are multiple electrodes in the atrium A (e.g., more than two) which would allow the system 1 to electronically search multiple atrial sensing vectors for the strongest signal. In a fourth embodiment, one of the feedthroughs 16 is eliminated by having one of the electrodes 41, 42, in the atrium A (the reference electrode) shorted to either the return ring electrode 12 or the housing 10 of the hermetic enclosure.

It is also possible to use this architecture to create a DDD pacing system. As long as the ring electrodes 41, 42 in the atrium A are near excitable tissue, pacing as well as sensing could be achieved with this configuration. In one embodiment, there are multiple electrodes (e.g., more than two) on the atrial lead extension 40. In this embodiment, the system 1 can electrically search multiple vectors to find the one with the lowest pacing threshold.

The presented intracardiac pacemaker device has the following advantages compared to already existing solutions: First of all, it supports VDD pacing mode, giving AV synchrony to intracardiac pacing. Furthermore, it contains a single array of feedthroughs 16 (e.g., one feedthrough array located at the proximal end of the hermetic housing). Further, it contains no tube through the battery 30 for electrical interconnects across the battery. Furthermore, it contains no wire on the outside of the hermetic housing 10 for electrical interconnects across the battery 30. Furthermore, it improves stability of the implant 1 (because the highest mass density component is located right by the anchor). Furthermore, it is extensible to multiple electrodes (e.g., more than the two in the preferred embodiment) and/or embedded sensors (e.g., temperature, acceleration, etc.) on the lead extension 40.

Further, it is extensible to a DDD system (atrial electrodes can pace as well as sense as long as they are near excitable tissue), and finally, it simplifies the pacing electrode interconnect by integration with the housing 10, reducing parts count and assembly time.

Furthermore, the following embodiments relate to anchoring and positioning of the elongated lead extension in the atrium A of the heart H.

Figure 5:
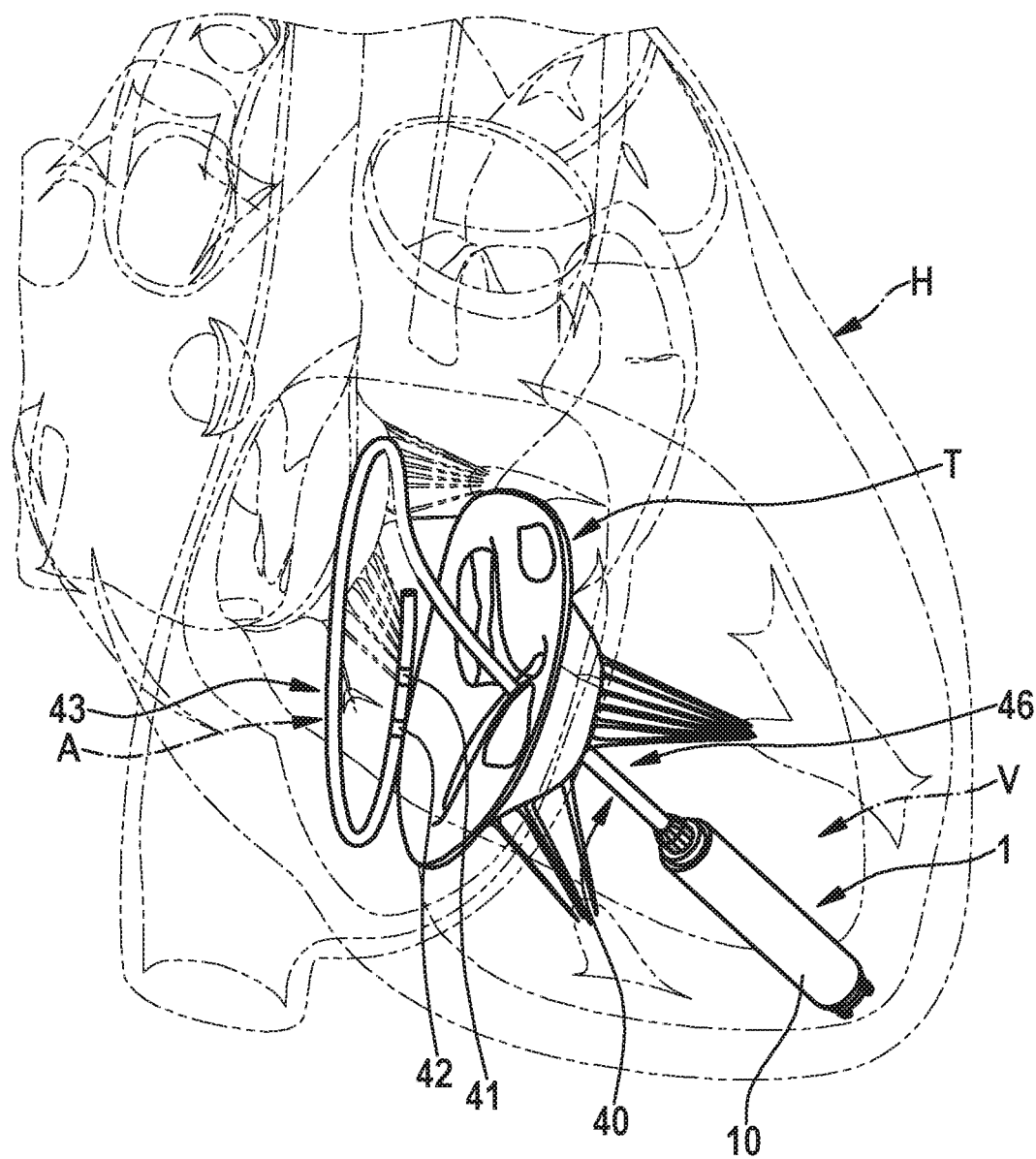
FIG. 5 shows an embodiment of the elongated lead extension comprising a shape memory alloy wire.
Figure 6:
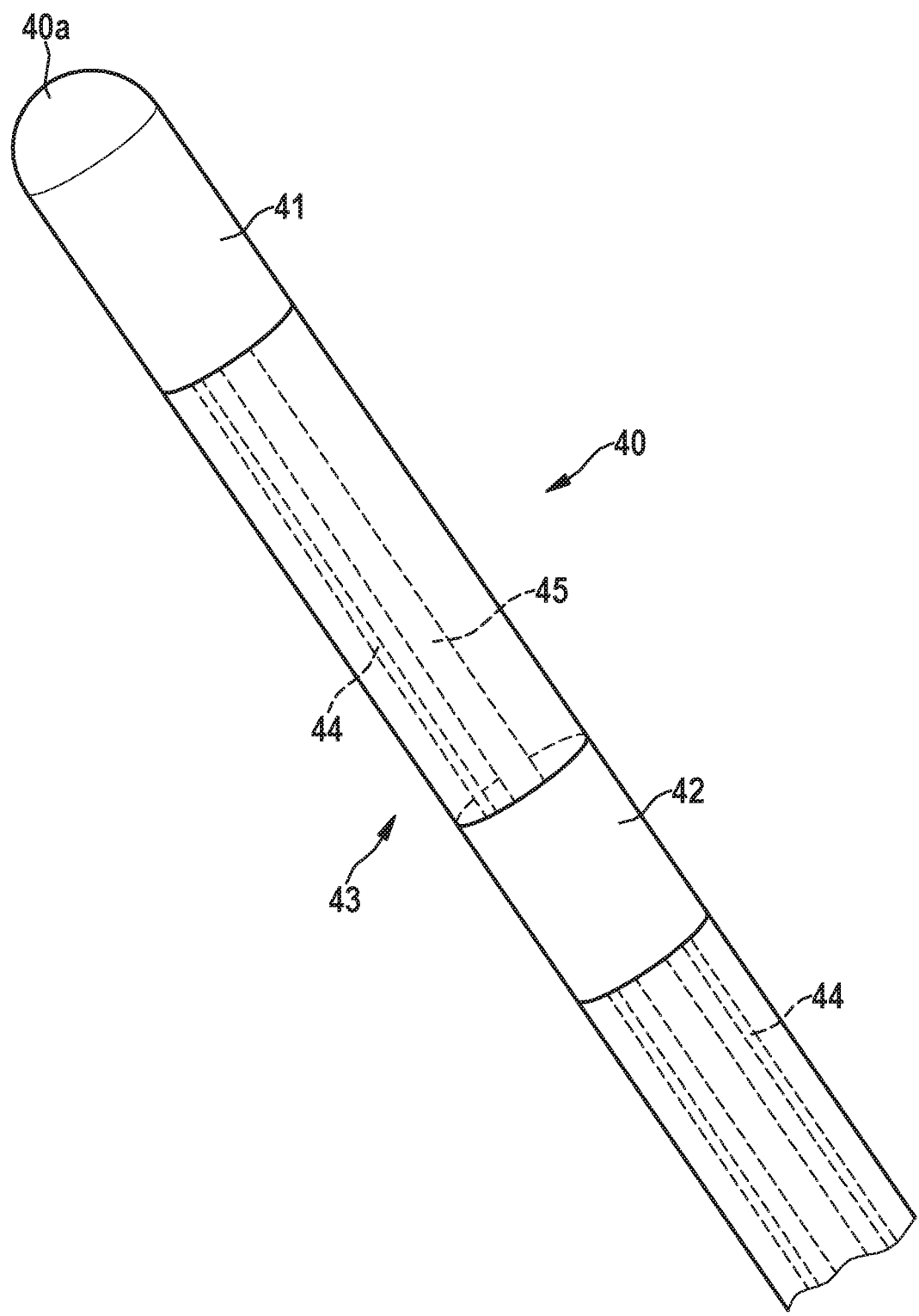
FIG. 6 shows a detail of an end of the elongated lead extension comprising a first and a second electrode for atrial sensing.

Particularly, according to an embodiment 1 shown in FIG. 5, the housing 10 in this embodiment of the intracardiac pacemaker device 1 is configured to be implanted in the right ventricle V. When housing 10 of the intracardiac pacemaker device 1 is implanted in the right ventricle V, the elongated lead extension 40 protrudes from the proximal end 10a of the housing 10, passes through the tricuspid valve T, and further extends into the right atrium A. Particularly, the elongated lead extension 40 is soft and compliant in its distal portion, but in its proximal portion 43 (the portion proximal to the implanter during implantation, which is the portion of the extension 40 farthest from the housing 10) it comprises a shape memory alloy wire 45 (cf. FIG. 6), such as a Nitinol wire, that is shape set to a circular configuration that partially circumnavigates the atrium A as shown in FIG. 5. This serves to keep the extension 40 in place in the atrium A. As shown in FIG. 6, the elongated lead extension 40 comprises at least one electrode, here particularly two electrodes 41, 42 in the proximal portion 43 of the lead extension 40, wherein the first electrode 41 is arranged at an end 40a of the lead extension 40. The two electrodes 41, 42 are connected via wires 44 to the electronic module 20, respectively, allowing the intracardiac leadless pacemaker 1 to differentially sense in the atrium as shown in FIG. 6.

One advantage of this embodiment is that the large circular shape of the (e.g., Nitinol) wire 45 forces the electrodes 41, 42 up against the cardiac tissue, and this may allow for atrial pacing as well as sensing. The soft, thin, and compliant distal portion 46 of the elongated lead extension 40 transverses the valve T in much the same way that a traditional right ventricular pacing lead chronically traverses the tricuspid valve T. In one embodiment, the distal portion 46 of the lead extension 40 (i.e., the portion closest to the pacemaker 1) is identical in construction and cross-section to traditional right ventricular pacing leads.

Figure 7:
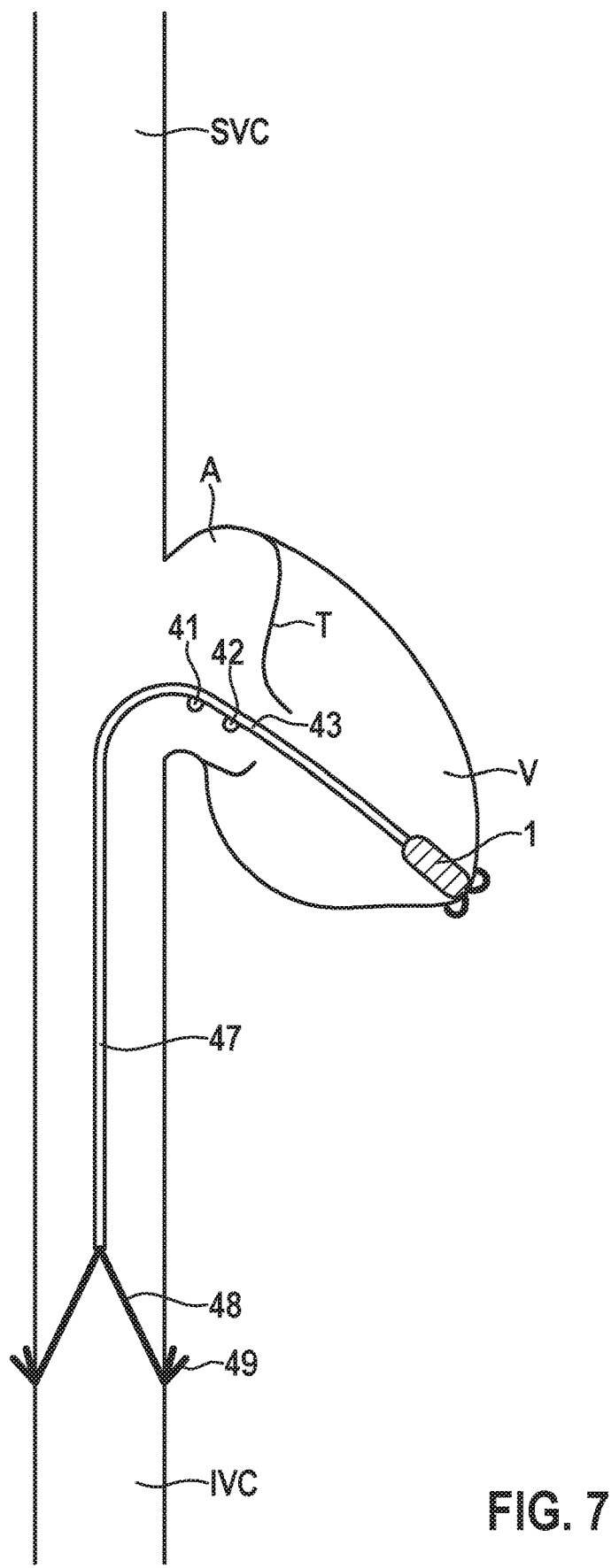
FIG. 7 shows a schematic illustration of an embodiment of an intracardiac pacemaker device comprising a tether and an anchor.

According to a further embodiment illustrated in FIG. 7, the intracardiac pacemaker device 1 comprises an anchor 48 that is configured to be deployed in the inferior vena cava (IVC) (or in an alternative embodiment in the superior vena cava (SVC)), wherein the anchor 48, together with a tether 47, act together to ensure that the electrodes 41, 42 of the elongate lead extension 40 stay in the atrium A. Particularly, the anchor 48 can be designed as a self-expanding stent like structure. In one embodiment it has small barbs 49 on it, to further secure it in place (cf. FIG. 7). In another embodiment the anchor 48 has no barbs, and is kept in place in the IVC by the radial force of the self-expanding anchor 48 that can comprise a stent structure (cf. FIG. 8). In all these embodiments, the IVC anchor has a tether 47 attached to it that ties the anchor 48 to the elongated lead extension 40 protruding from the housing 10 of the pacemaker 1 (as shown in FIG. 7). The tether 47 keeps the first electrode 41 of the lead extension 40 in the atrium A by applying tension to resist the flow of blood. In one embodiment the tether 47 is made of non-absorbable surgical suture material such as nylon, polyester, PVDF and polypropylene.

Figure 8:
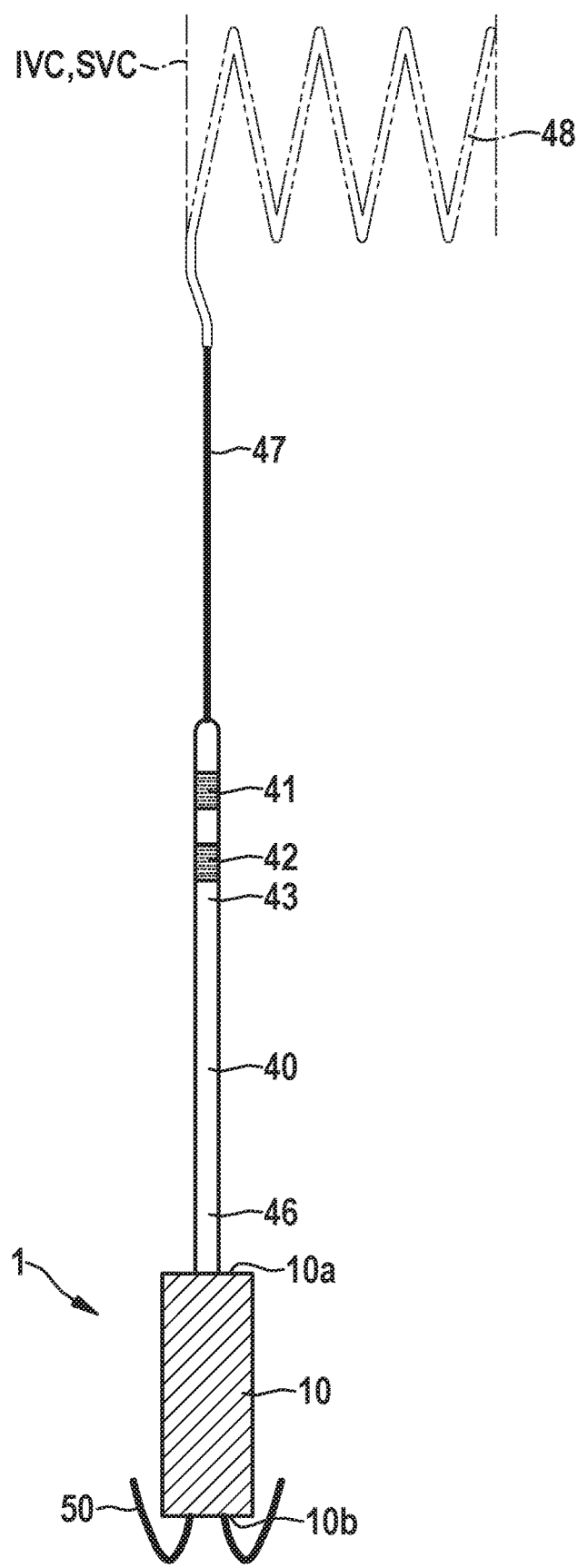
FIG. 8 shows a schematic illustration of an alternative embodiment of an intracardiac pacemaker device having a tether and an anchor.
Figure 9:
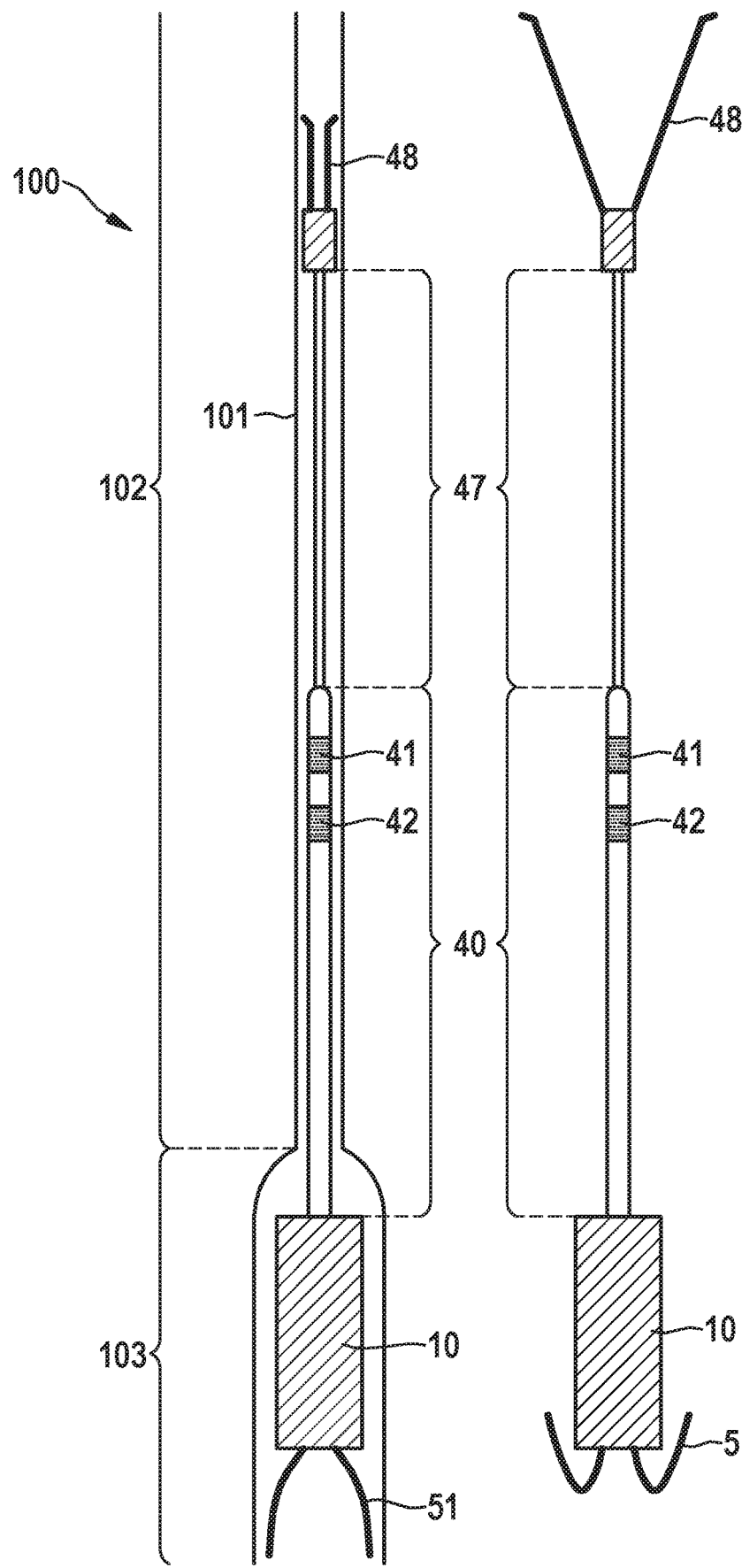
FIG. 9 shows an embodiment of a delivery system for implantation of an intracardiac pacemaker device.

A delivery system 100 for the implant 1 described in conjunction with FIGS. 7 and 8 is illustrated in FIG. 9. The delivery system 100 comprises a catheter 101 that, in the preferred embodiment, is inserted into the venous system through femoral access. The delivery system catheter 101 is then maneuvered up through the IVC to the atrium A, then through the tricuspid valve T to the ventricle V. In one embodiment the delivery catheter 101 is steerable. The catheter 101 is pre-loaded with the intracardiac pacemaker device 1 in a cup 103 at the distal end, with the IVC anchor 48 residing in the catheter lumen 102 proximal to the pacemaker device 1 and held in a compact, compressed state by the catheter (as shown in FIG. 9). In one embodiment the pacemaker 1 has nitinol tines 51 for fixation to a cardiac wall. The tines 51 are exposed when the catheter cup 103 is pulled back. The implanted configuration is shown on the right hand side of FIG. 9.

Figure 10:
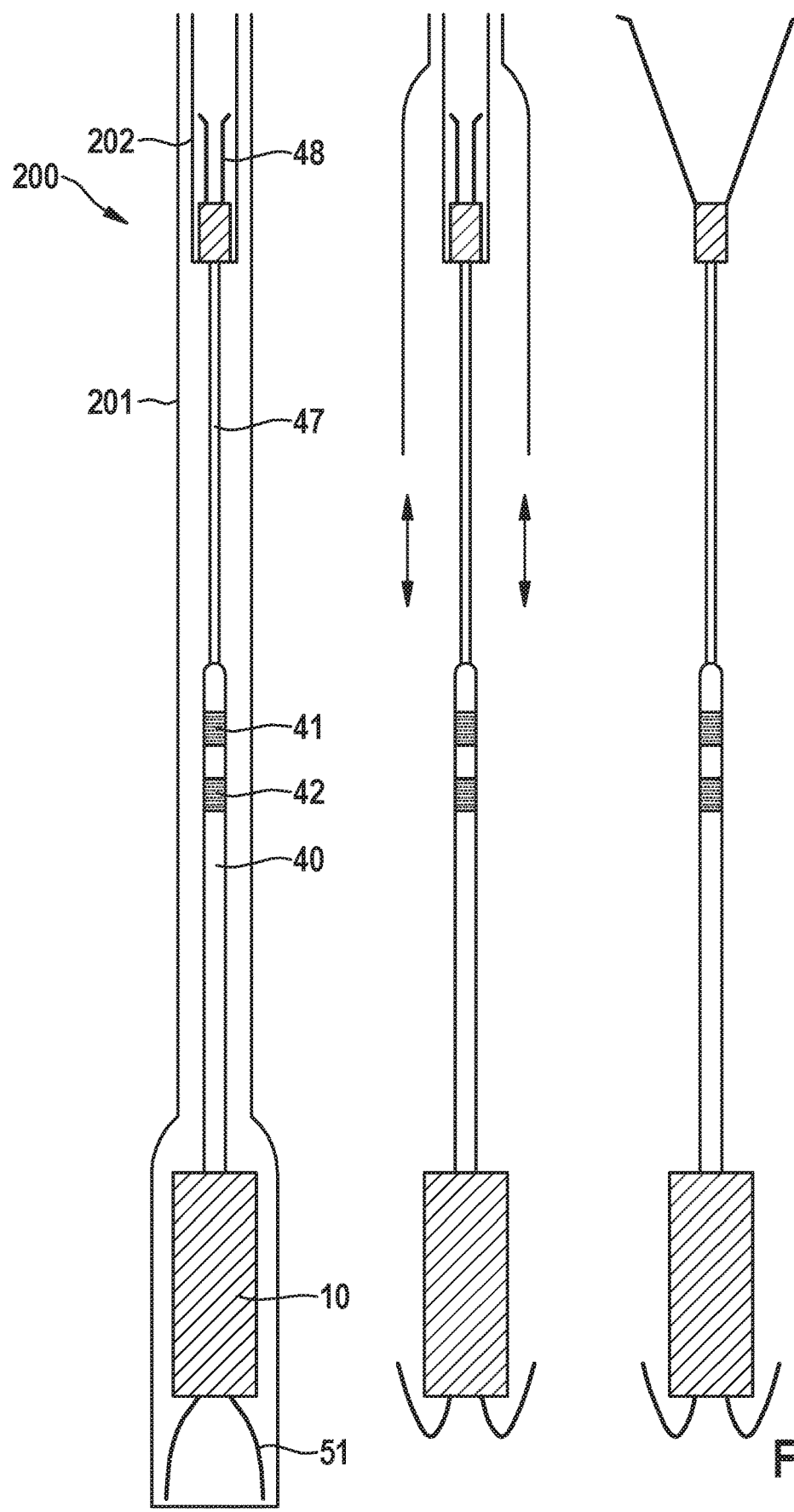
FIG. 10 shows a further embodiment of a delivery system for implantation of an intracardiac pacemaker device.

FIG. 10 shows a two-catheter embodiment of the delivery system 200 in various stages of implant deployment. The left image shows the delivery tool 200 with the device 1 loaded in it prior to deployment. The middle shows the delivery tool 200 with the pacemaker 1 deployed, but the IVC anchor 48 not yet deployed. This stage of partial deployment is called "tether mode". It allows the pacemaker 1 to pace the heart H, for pacing thresholds to be measured, for sensing amplitude to be checked, and for electrode impedance to be measured, all without deploying the IVC anchor 48. Should the pacing parameters measured in tether mode be inadequate, the intracardiac pacemaker device 1 can be retracted back into the delivery catheter 200 and re-deployed in a different position. Once an implant position is found with acceptable pacing parameters, then the device 1 and IVC anchor 48 is fully deployed by first withdrawing the outer catheter 201 (deploying the leadless pacemaker and atrial extension), then positioning the IVC anchor 48 to its desired location (as seen on floro), then finally deploying the IVC anchor 48 by pulling back on the inner catheter 202. This fully deployed state is illustrated on the right of FIG. 10.

Figure 11:
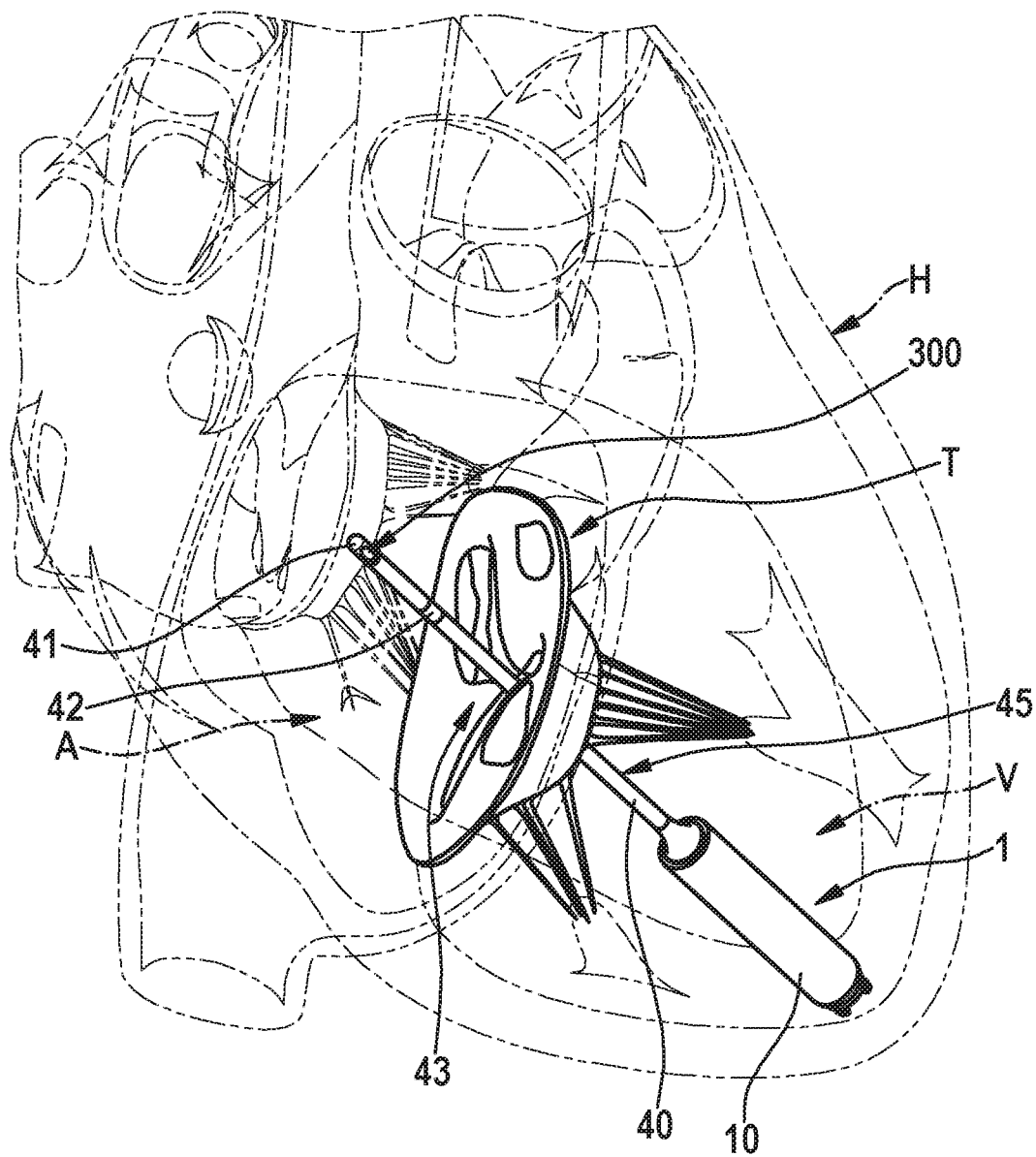
FIG. 11 shows a further embodiment of an intracardiac pacemaker device having a recapturing structure for removing the device from the implantation site.

According to a further embodiment shown in FIG. 11, the elongated lead extension 40 has a shape memory wire 45, particularly a Nitinol wire, throughout its entire length. The wire 45 is shape set to extend the lead extension 40 up through the valve T and into the atrium A. In one embodiment the extension is shape set to be straight, and in another embodiment it is shape set to have a gentle curve. In either embodiment the shape memory wire 45 is large enough that it causes the elongated lead extension 40 to resist the flow of blood and other forces (gravity, heat, movement, etc.) and permanently cross the tricuspid valve T and keep the electrodes 41, 42 up in the atrium A. Should the lead extension 40 ever migrate down into the ventricle V, the shape set wire 45 will bias the elongated lead extension 40 back to its extended position, resulting in it gently moving back up into the atrium A.

Figure 12:
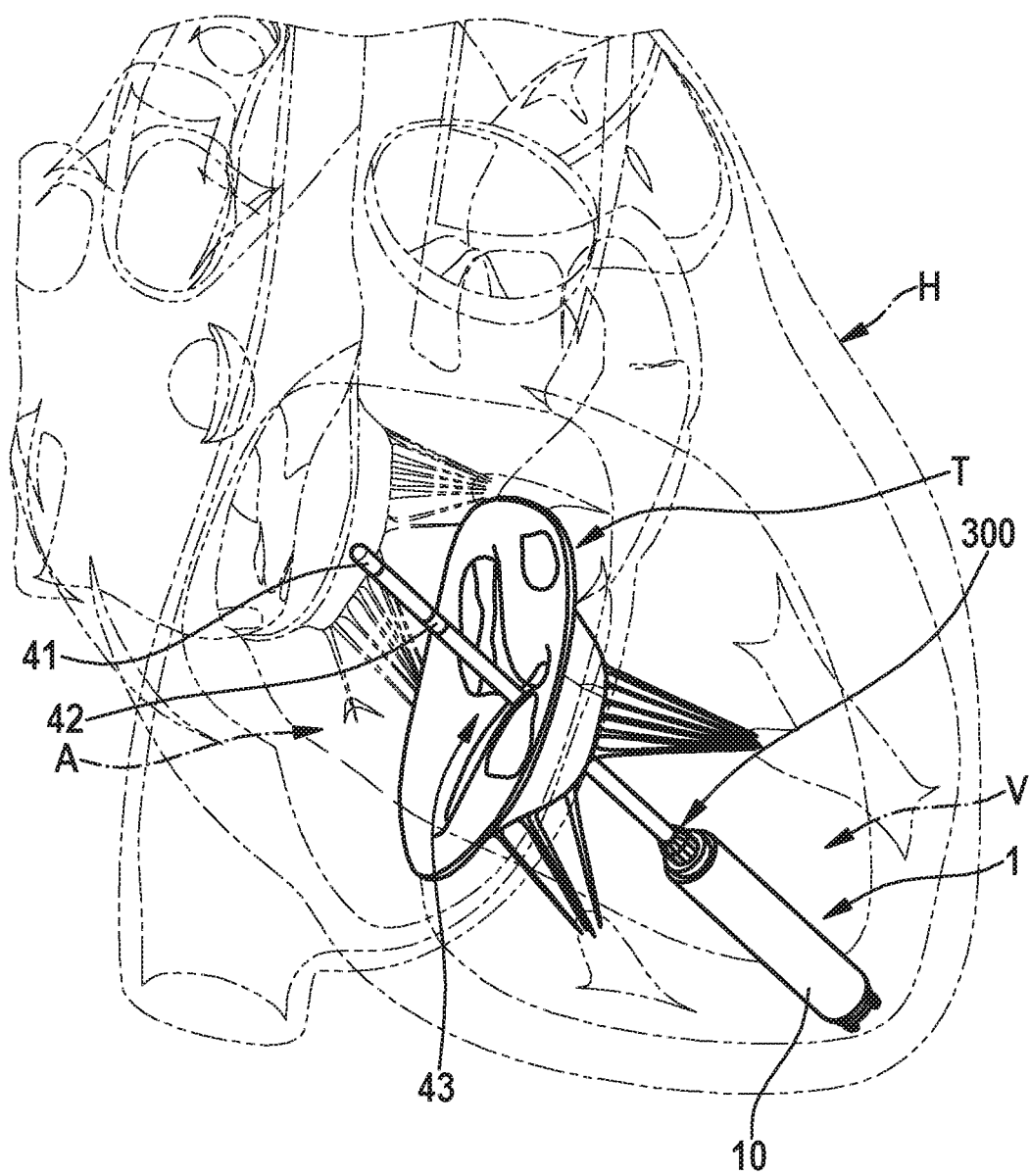
FIG. 12 shows a further embodiment of an intracardiac pacemaker device having a recapturing structure for removing the device from the implantation site.
Figure 13:
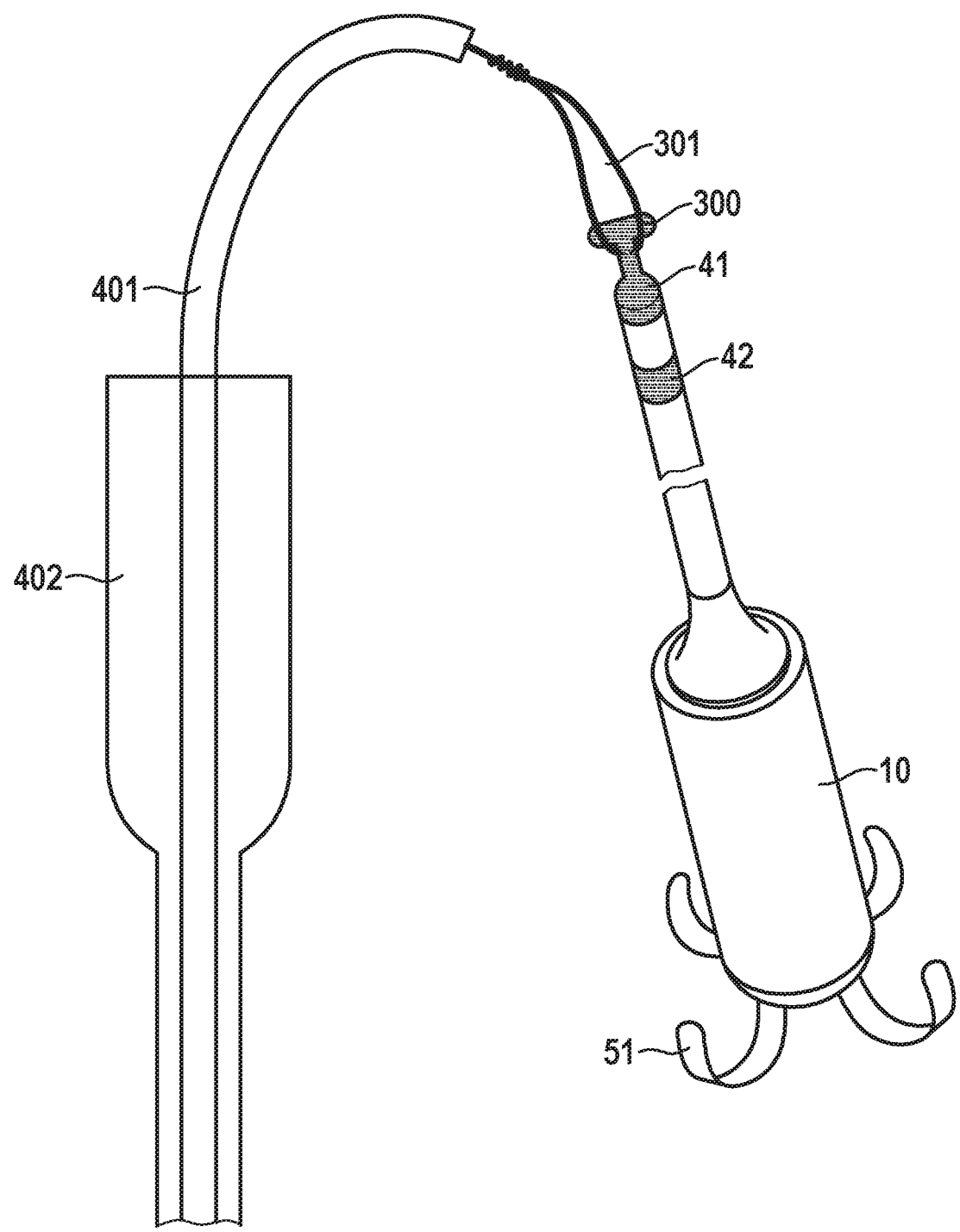
FIG. 13 shows a schematic illustration of a tool for explanting an intracardiac pacemaker device upon snaring of the device.
Figure 14:
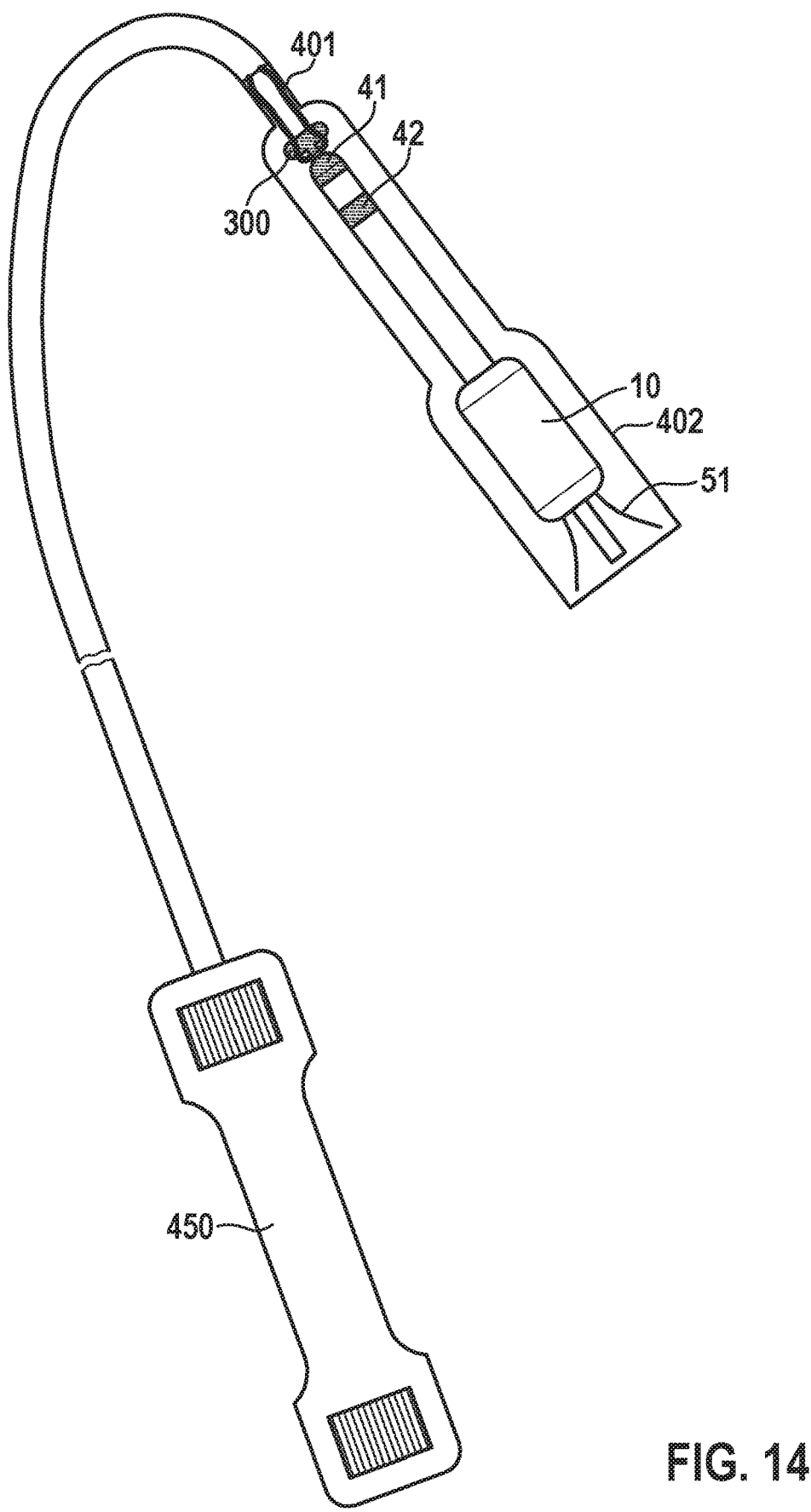
FIG. 14 shows a schematic illustration of a tool for explanting an intracardiac pacemaker device, wherein the intracardiac pacemaker device has been arranged in the tool for explantation.

In the preferred embodiment, the implantable leadless pacemaker system has a feature 300 to allow it to be snared for recapture. In one embodiment this snaring feature 300 is at the proximal end 40a of the elongated lead extension as shown in FIG. 11. In a second embodiment the snaring feature 300 is at the proximal portion of the hermetic housing 10 as shown in FIG. 12. In one embodiment the snaring feature 300 is a small hook structure, and in another embodiment it is a T-shaped structure. During explantation of a fully deployed device 1, the snaring feature 300 is first snared as shown in FIG. 13 using a snare 301, then an inner catheter 401 of an explantation catheter 400 (with a handle 450) similar to the implantation catheter 200 is advanced up over the snare 301 towards the implant 1. This inner catheter 401 cinches the snare loop tightly around the snaring feature 300. The outer catheter 402 is then advanced over the inner catheter 401, and then advanced over the pacemaker 1. The snare 301 is then used to disengage the pacemaker 1 from the cardiac tissue by pulling back on the snare while the outer catheter 402 gently pushes back against the cardiac tissue that the pacemaker 1 is being pulled out of the tissue (cf. FIG. 14). The explantation procedure is slightly more complicated for the system with the IVC anchor 48. In this embodiment, the IVC anchor 48 first needs to either be abandoned or re-captured. In one embodiment the IVC anchor 48 has a feature to allow it to be snared. Once snared, the IVC anchor 48 is designed to collapse and be pulled back into a catheter. At this point the explantation catheter is advanced up over the tether 47 towards the lead extension 40, then it continues to be advanced up over the lead extension and finally over the pacemaker 1. The snare 301 is then used to disengage the pacemaker 1 from the cardiac tissue by pulling back on the snare while the outer catheter 402 gently pushes back against the cardiac tissue. Alternatively, once the IVC anchor is pulled into the catheter, a cutting tool can then cut the tether 47 and the IVC anchor 48 can be removed from the vasculature. At that point the rest of the pacemaker 1 can be removed following the procedure outlined above for pacemakers 1 with lead extension 40 without IVC anchors 48.

Regardless of the implant embodiment adopted, beyond the local (likely bipolar) sensing support afforded within the atrium A, the atrial lead extension 40 provisions a means for accessing a more global surface-like e-gram. Such support arrives through the realization of an added option for a longer sensing vector that spans from the tip 40a of the atrial lead extension 40 to either the device housing 10 or pacing electrode 11. This longer vector, aligned with the long axis of the heart H, would facilitate accrual of more morphologically-enriched signal collection. Enriched data collection of this type would, in turn, offer meaningful interfaces for improved clinical care decisions. As an added bonus, any communication with the implant reliant upon e-field-based strategies would further benefit from this longer vector as the expanded vector could effectively serve as a functional antenna for such engagements. Furthermore, the present disclosure allows the pacemaker 1 to sense in the atrium A and give VDD and/or VDDR pacing therapy.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:
1. An intracardiac pacemaker device, comprising:
a housing comprising a proximal end and a distal end, the housing configured to be implanted entirely within a ventricle of a heart, and wherein the housing is made entirely of a conductive material,
an electronic module for generating pacing pulses arranged in the housing at a proximal end,
a battery for supplying energy to the electronic module arranged in the housing at a distal end,
an elongated lead extension protruding from the housing, at least a first electrode arranged on the elongated lead extension protruding from the proximal end of the housing, and a pacing electrode arranged at the distal end of the housing and a return electrode for applying said pacing pulses to cardiac tissue, wherein the pacing electrode is connected to the housing, wherein the electronic module is electrically coupled to the pacing electrode via only the housing, wherein the electronic module is configured to carry out measurements of electrical activity via the at least one first electrode of the elongated lead extension, and wherein the electronic module is electrically coupled to the at least one first electrode of the elongated lead extension via at least one electrical feedthrough.

2. The intracardiac pacemaker device according to claim 1, wherein the housing is partly coated with an electrically insulating material.

3. The intracardiac pacemaker device according to claim 1, wherein the housing is formed by a separate electronics housing enclosing the electronic module and a separate battery housing of the battery, wherein the electronics housing is connected to the battery housing, wherein the electronics housing forms a proximal portion of the housing of the pacemaker device comprising said proximal end of the housing of the pacemaker device, and wherein the battery housing forms a distal portion of the housing of the pacemaker device comprising said distal end of the housing.

4. The intracardiac pacemaker device according to claim 3, wherein the electronics housing is connected to the battery housing by a welding seam.

5. The intracardiac pacemaker device according to claim 3, wherein the battery comprises a first and a second terminal connected to the electronic module, respectively, wherein the first terminal is formed by the battery housing and the second terminal is formed by a feedthrough pin.

6. The intracardiac pacemaker device according to claim 1, wherein the return electrode is electrically isolated from the housing, wherein the return electrode is arranged on the proximal end of the housing or on the elongate lead extension.

7. The intracardiac pacemaker according to claim 1, wherein the intracardiac pacemaker further comprises a second electrode arranged on the elongated lead extension.

8. The intracardiac pacemaker according to claim 1, wherein the intracardiac pacemaker device further comprises a plurality of electrodes arranged on the elongated lead extension.

9. The intracardiac pacemaker device according to claim 1, wherein the intracardiac pacemaker device further comprises at least two feedthroughs at the proximal end of the housing for electrically connecting the return electrode and the at least one first electrode to the electronic module.

10. The intracardiac pacemaker device according to claim 1, wherein the intracardiac pacemaker device further comprises at least three feedthroughs at the proximal end of the housing for electrically connecting the return electrode and the at least one first electrode and the second electrode to the electronic module.

11. The intracardiac pacemaker device according to claim 1, wherein the intracardiac pacemaker device further comprises a plurality of feedthroughs at the proximal end of the housing for electrically connecting the return electrode and said plurality of electrodes of the elongated lead extension to the electronic module.

12. The intracardiac pacemaker device according to claim 1, wherein the pacing electrode is electrically connected via a pin to the distal end of the housing.

13. The intracardiac pacemaker device according to claim 1, wherein the pacing electrode is integrally formed with the distal end of the housing.

14. The intracardiac pacemaker device according to claim 1, wherein the intracardiac pacemaker device comprises a tine array for anchoring the housing to cardiac tissue, which tine array is connected to the distal end of the housing.

15. The intracardiac pacemaker device according to claim 14, wherein the intracardiac pacemaker device comprises an electrically isolating ring element for connecting the tine array to the distal end of the housing, wherein said ring element surrounds the pacing electrode which is arranged in a central opening of the ring element.

* * * * *